(12) United States Patent
Pampaloni et al.

(10) Patent No.: US 8,772,521 B2
(45) Date of Patent: Jul. 8, 2014

(54) METAL ALKYL-ARENES AND PROCESSES FOR THE PREPARATION THEREOF

(75) Inventors: Guido Pampaloni, Pontedera (IT); Filippo Renili, Pisa (IT); Anna Sommazzi, Santa Margherita-Genoa (IT); Fabio Marchetti, Pisa (IT); Francesco Masi, Sant Angelo Lodigiano-Lodi (IT); Mario Polesello, Ferrara (IT)

(73) Assignee: Versalis S.p.A., San Donato Milanese (IT)

( * ) Notice: Subject to any disclaimer, the term of this patent is extended or adjusted under 35 U.S.C. 154(b) by 0 days.

(21) Appl. No.: 13/996,842

(22) PCT Filed: Dec. 23, 2011

(86) PCT No.: PCT/EP2011/073925
§ 371 (c)(1),
(2), (4) Date: Jul. 23, 2013

(87) PCT Pub. No.: WO2012/089652
PCT Pub. Date: Jul. 5, 2012

(65) Prior Publication Data
US 2013/0296592 A1 Nov. 7, 2013

(30) Foreign Application Priority Data
Dec. 27, 2010 (IT) ............................. MI2010A2400

(51) Int. Cl.
*C07F 19/00* (2006.01)
*B01J 31/12* (2006.01)
*B01J 31/00* (2006.01)
*C08F 4/42* (2006.01)

(52) U.S. Cl.
CPC . *C07F 19/00* (2013.01); *C08F 4/42* (2013.01); *B01J 31/122* (2013.01)
USPC .............................. 556/27; 526/113; 502/153

(58) Field of Classification Search
CPC ............ C07F 19/00; C08F 4/42; B01J 31/122
USPC .............................. 556/27; 502/153; 523/113
See application file for complete search history.

(56) References Cited

PUBLICATIONS

Calderazzo, Fausto, et al., Heavier Halides of Early Transition Elements by Halide-Exchange Reactions. Crystal and Molecular Structure of [Ph3C]2[Hf2Cl]0], Dalton Transaction, RSC Publishing, Cambridge GB, No. 9, Jan. 1, 1990, pp. 2743-2746.
Calderazzo, Fausto, et al. "Arene Derivatives of Zirconium(II) and Hafnium(II)", Journal of the Chemical Society, Dalton Transactions: Inorganic Chemistry, 1990, pp. 1813-1818.
Calderazzo, Fausto, et al., "Reactions of Zr(.hepta.6-benzyne)(A1C14)2 with alkynes: Cycloologomerization Reactions and Crystals and Molecular Structure of the Seven-Membeered Metallacycle [ZrCPh(CPh)4CPh][(.mu.-C1) 2A1C12]2", Organometallics, vol. 10, No. 4, 1991, pp. 896-901.

*Primary Examiner* — Porfirio Nazario Gonzalez
(74) *Attorney, Agent, or Firm* — Tarolli, Sundheim, Covell & Tummino LLP

(57) ABSTRACT

Metal alkyl-arene having general formula (I) or (Ia): M ($\eta^6$-arene)$_2$Al$_q$X$_r$R$_s$ (I) M ($\eta^6$-arene)Al$_q$X$_r$R$_s$ (Ia) wherein: —M represents zirconium (Zr), hafnium (Hf), or mixtures thereof, preferably zirconium; —arene represents a benzene, or a benzene 10 substituted with from 1 to 6 linear or branched $C_1$-$C_6$ alkyl groups, or mixtures thereof; —X represents a halogen atom selected from chlorine, bromine, fluorine, iodine, preferably chlorine; —R represents a linear or branched $C_1$-$C_{15}$ alkyl group; —q is a number ranging from 2 to 6, preferably 3 for a metal alkyl-arene having general formula (I), 2 for a metal alkyl-arene having general formula (Ia); —r is a number ranging from 1 to 20, preferably 9 for a metal alkyl-arene having general formula (I), 6 for a metal alkyl-arene having general formula (Ia); —s is a number ranging from 1 to 6, preferably 2. Said metal alkyl-arene can be advantageously used for the preparation of solid components of catalysts for the (co)polymerization of α-olefins.

20 Claims, No Drawings

METAL ALKYL-ARENES AND PROCESSES FOR THE PREPARATION THEREOF

RELATED APPLICATION

This application is a National Phase filing of PCT/EP2011/073925, filed Dec. 23, 2011, and claims priority to Italian Application No. MI2010A002400, filed Dec. 27, 2010, the subject matter of which are incorporated herein by reference in their entirety.

The present invention relates to a metal alkyl-arene.

More specifically, the present invention relates to a metal alkyl-arene comprising at least one halogen atom.

The present invention also relates to a solution or to an oil comprising said metal alkyl-arene.

Furthermore, the present invention also relates to processes for the preparation of said metal alkyl-arene, as well as of said solution or of said oil comprising said metal alkyl-arene.

Said metal alkyl-arene can be advantageously used for the preparation of solid catalyst components for the (co)polymerization of α-olefins.

Metal arenes comprising at least one halogen atom are known in literature.

As specified, for example, in the article of Calderazzo F. et al. "Arene Derivatives of Zirconium(II) and Hafnium(II), published in "*Journal of the Chemical Society Dalton Transactions*" (1990), pages 1813-1817, or by Pampaloni G. in the review "Aromatic hydrocarbons as ligand. Recent advances in the synthesis, the reactivity and the applications of bis($\eta^6$-arene) complexes", published in "*Coordination Chemistry Reviews*" (2010), Vol. 254, pages 402-419, it is possible to obtain metal arenes comprising at least one halogen atom, wherein the metal is present in a low oxidation state (e.g., in the bivalent state), by means of a reaction which provides the reduction according to Fischer-Hafner of a metal halide having general formula $MX_4$, wherein M is an atom of titanium, zirconium or hafnium and X is a halogen atom selected from chlorine, bromine, iodine, by means of the aluminium metal/aluminium halide Al/AlX$_3$ system, wherein X is a halogen atom selected from chlorine, bromine, iodine, according to the following equation:

$$3MX_4 + 2Al + 4AlX_3 + 3\text{ arene} \rightarrow 3M(\eta^6\text{-arene})(AlX_4)_2.$$

Metal arenes soluble in the reaction medium, or biphasic systems in which there is a heavier, highly coloured phase, substantially containing the whole metal arene, and a slightly coloured overlying phase wherein only traces of said metal arene are present, can be obtained depending on the molar ratios between the aluminium present in the compound $AlX_3$ and the metal present in the compound $MX_4$, and/or the type of arene used in the above-mentioned reaction.

Titanium arenes having general formula:

$$Ti(\eta^6\text{-arene})(AlX_4)_2$$

wherein X is a halogen atom selected from chlorine, bromine, iodine, are generally soluble in the reaction medium and can be easily isolated from said reaction medium by crystallization, whereas zirconium arenes having general formula:

$$Zr(\eta^6\text{-arene})(AlX_4)_2$$

and hafnium arenes having general formula:

$$Hf(\eta^6\text{-arene})(AlX_4)_2$$

wherein X is a halogen atom selected from chlorine, bromine, iodine, form oils from which it is difficult to isolate said zirconium arenes and/or hafnium arenes. Furthermore, it is difficult to use said oils as such, in particular in the preparation of solid catalyst components.

In the above-mentioned known art, no mention is made of the possibility of obtaining metal alkyl-arenes.

The Applicant has considered the problem of finding metal alkyl-arenes which can be isolated from the reaction medium (by means of precipitation in an organic solvent, for example) or, in any case, capable of forming solutions or oils comprising said metal alkyl-arenes which can be used as such, in particular for the preparation of solid catalyst components for the (co)polymerization of α-olefins.

The Applicant has now found metal alkyl-arenes with the metal in the bivalent state, comprising at least one halogen atom, which can be isolated from the reaction medium (by means of precipitation in an organic solvent, for example), or capable of forming solutions or oils comprising said metal alkyl-arenes which can be used as such. Said metal alkyl-arenes, as well as said solutions or said oils comprising said metal alkyl-arenes, can be advantageously used for the preparation of solid catalyst components for the (co)polymerization of α-olefins.

An object of the present invention therefore relates to a metal alkyl-arene having general formula (I) or (Ia):

$$M(\eta^6\text{-arene})_2Al_qX_rR_s \qquad (I)$$

$$M(\eta^6\text{-arene})Al_qX_rR_s \qquad (Ia)$$

wherein:

M represents zirconium (Zr), hafnium (Hf), or mixtures thereof, preferably zirconium;

arene represents a benzene, or a benzene substituted with from 1 to 6 linear or branched $C_1$-$C_6$ alkyl groups, or mixtures thereof;

X represents a halogen atom selected from chlorine, bromine, fluorine, iodine, preferably chlorine;

R represents a linear or branched $C_1$-$C_{15}$ alkyl group;

q is a number ranging from 2 to 6, preferably 3 for a metal alkyl-arene having general formula (I), 2 for a metal alkyl-arene having general formula (Ia);

r is a number ranging from 1 to 20, preferably 9 for a metal alkyl-arene having general formula (I), 6 for a metal alkyl-arene having general formula (Ia);

s is a number ranging from 1 to 6, preferably 2.

For the purposes of the present description and of the following claims, the definitions of the numerical ranges always include the extremes, unless otherwise specified.

For the purposes of the present description and of the following claims, the terms "mole" and "molar ratio" are used both for compounds consisting of molecules and for atoms and ions, omitting for the latter the term gram atom or atomic ratio, even if scientifically more correct.

In accordance with a preferred embodiment of the present invention, in the metal alkyl-arene having general formula (I) or (Ia), said arene can be selected from: benzene, toluene, ortho-xylene, meta-xylene, para-xylene, 1,2,3-trimethylbenzene, 1,2,4-trimethylbenzene, 1,3,5-trimethylbenzene (mesitylene), hexamethylbenzene, or mixtures thereof. Benzene, toluene, 1,3,5-trimethylbenzene (mesitylene) are preferred.

In accordance with a preferred embodiment of the present invention, in the metal alkyl-arene having general formula (I) or (Ia), said group R can be selected from: ethyl, n-propyl, iso-propyl, n-butyl, sec-butyl, tert-butyl, iso-butyl, n-pentyl, n-hexyl, n-heptyl, n-octyl, n-decyl, n-tridecyl. Ethyl, n-butyl, sec-butyl, iso-butyl, n-pentyl, n-octyl, n-tridecyl, are preferred.

Specific examples of the metal alkyl-arene having general formula (I) or (Ia) object of the present invention are:
Zr($\eta^6$-benzene)$_2$Al$_3$Cl$_9$(n-butyl)$_2$;
Zr($\eta^6$-benzene)$_2$Al$_3$Cl$_9$(n-octyl)$_2$;
Zr($\eta^6$-mesitylene)$_2$Al$_3$Cl$_9$(butyl)$_2$;
Zr($\eta^6$-mesitylene)$_2$Al$_3$Cl$_9$(n-octyl)$_2$;
Zr($\eta^6$-toluene)$_2$Al$_3$Cl$_9$(butyl)$_2$;
Zr($\eta^6$-toluene)$_2$Al$_3$Cl$_9$(n-octyl)$_2$;
Zr($\eta^6$-benzene)Al$_2$Cl$_6$(n-octyl)$_2$;
Zr($\eta^6$-benzene)Al$_2$Cl$_3$(n-octyl)$_5$;
Zr($\eta^6$-benzene)Al$_2$Cl$_5$(n-octyl)$_3$;
Zr($\eta^6$-benzene)Al$_2$Cl$_4$(n-octyl)$_4$;
Zr($\eta^6$-toluene)Al$_2$Cl$_6$(n-octyl)$_2$;
Zr($\eta^6$-toluene)Al$_2$Cl$_3$(n-octyl)$_5$;
Zr($\eta^6$-toluene)Al$_2$Cl$_5$(n-octyl)$_3$;
Zr($\eta^6$-toluene)Al$_2$Cl$_4$(n-octyl)$_4$;
Zr($\eta^6$-mesitylene)Al$_2$Cl$_6$(n-octyl)$_2$;
Zr($\eta^6$-mesitylene)Al$_2$Cl$_3$(n-octyl)$_5$;
Zr($\eta^6$-mesitylene)Al$_2$Cl$_5$(n-octyl)$_3$;
Zr($\eta^6$-mesitylene)Al$_2$Cl$_4$(n-octyl)$_4$;
Zr($\eta^6$-benzene)Al$_2$Cl$_6$(n-butyl)$_2$;
Zr($\eta^6$-benzene)Al$_2$Cl$_6$(iso-butyl)$_2$;
Zr($\eta^6$-benzene)Al$_2$Cl$_3$(n-butyl)$_5$;
Zr($\eta^6$-benzene)Al$_2$Cl$_5$(n-butyl)$_3$;
Zr($\eta^6$-benzene)Al$_2$Cl$_4$(n-butyl)$_4$;
Zr($\eta^6$-benzene)Al$_2$Cl$_4$(ethyl)$_4$;
Zr($\eta^6$-toluene)Al$_2$Cl$_6$(n-butyl)$_2$;
Zr($\eta^6$-toluene)Al$_2$Cl$_3$(n-butyl)$_5$;
Zr($\eta^6$-toluene)Al$_2$Cl$_5$(n-butyl)$_3$;
Zr($\eta^6$-toluene)Al$_2$Cl$_4$(n-butyl)$_4$;
Zr($\eta^6$-mesitylene)Al$_2$Cl$_6$(n-butyl)$_2$;
Zr($\eta^6$-mesitylene)Al$_2$Cl$_6$(sec-butyl)$_2$;
Zr($\eta^6$-mesitylene)Al$_2$Cl$_6$(iso-butyl)$_2$;
Zr($\eta^6$-mesitylene)Al$_2$Cl$_6$(n-pentyl)$_2$;
Zr($\eta^6$-mesitylene)Al$_2$Cl$_6$(ethyl)$_2$;
Zr($\eta^6$-mesitylene)Al$_2$Cl$_3$(n-butyl)$_5$;
Zr($\eta^6$-mesitylene)Al$_2$Cl$_5$(n-butyl)$_3$;
Zr($\eta^6$-mesitylene)Al$_2$Cl$_4$(n-butyl)$_4$.

In a further aspect, the present invention also relates to a process for the preparation of a metal alkyl-arene having general formula (I) or (Ia) which comprises reacting the following components:
(i) at least one metal halide having general formula (II):

$$MX_4 \qquad (II)$$

wherein:
M represents zirconium (Zr), hafnium (Hf), or mixtures thereof, preferably zirconium;
X represents a halogen atom selected from chlorine, bromine, fluorine, iodine, preferably chlorine;
(ii) metallic aluminium;
(iii) optionally, at least one aluminium halide having general formula (III):

$$AlX_3 \qquad (III)$$

wherein:
X represents a halogen atom selected from chlorine, bromine, iodine, preferably chlorine;
(iv) at least one arene;
(v) at least one alkylating agent selected from:
metal alkyls having general formula (IV):

$$M_1(R_1)_m \qquad (IV)$$

wherein:
$M_1$ represents aluminium, magnesium, zinc, lithium; $R_1$ represents a linear or branched $C_1$-$C_{20}$, preferably $C_1$-$C_{18}$, alkyl group; m is 1, 2 or 3;

aluminium alkyl chlorides having general formula (V):

$$Al(R_2)_nCl_{3-n}$$

wherein $R_2$ represents a linear or branched $C_1$-$C_{20}$, preferably $C_1$-$C_{18}$ alkyl group; n is 1 or 2.

According to a preferred embodiment of the present invention, said arene can be selected from: benzene, toluene, ortho-xylene, meta-xylene, para-xylene, 1,2,3-trimethylbenzene, 1,2,4-trimethylbenzene, 1,3,5-trimethylbenzene (mesitylene), hexamethylbenzene, or mixtures thereof. Benzene, toluene, 1,3,5-trimethylbenzene (mesitylene), or mixtures thereof, are preferred.

According to a preferred embodiment of the present invention, said metal alkyls can be selected from: lithium n-butyl, lithium sec-butyl, lithium tert-butyl, lithium iso-butyl, lithium n-pentyl, aluminium tri-ethyl, aluminium tri-iso-butyl, aluminium tri-octyl, butyl-octyl-magnesium, or mixtures thereof.

According to a preferred embodiment of the present invention, said aluminium alkyl chlorides can be selected from: di-ethyl-aluminium chloride, mono-ethyl-aluminium dichloride, n-octyl aluminium dichloride, di-methyl-aluminium chloride, di-isobutyl-aluminium chloride, iso-butyl-aluminium dichloride, ethyl-aluminium sesquichloride, or mixtures thereof.

According to a preferred embodiment of the present invention, said process can be carried out by operating with a molar ratio between the aluminium present in the aluminium halide having general formula (III) and the metal present in the metal halide having general formula (II), ranging from 1 to 4, preferably from 1.5 to 3.

According to a further preferred embodiment of the present invention, said process can be carried out by operating with a molar ratio, between the metal present in the metal alkyls having general formula (IV) and the metal present in the metal halide having general formula (II), ranging from 0.5 to 10, preferably from 1 to 2.

According to a further preferred embodiment of the present invention, said process can be carried out by operating with a molar ratio, between the aluminium present in the aluminium alkyl chlorides having general formula (V) and the metal present in the metal halide having general formula (II), ranging from 1 to 6, preferably from 2 to 3.

According to a preferred embodiment of the present invention, said process can be carried out in the presence of an organic solvent, preferably an aliphatic or aromatic hydrocarbon solvent such as, for example, n-pentane, n-hexane, mixtures of hexanes, n-heptane, n-octane, n-nonane, n-decane, n-undecane, n-dodecane, benzene, toluene, xylene, 1,3,5,-trimethylbenzene (mesitylene).

According to a preferred embodiment of the present invention, said process can be carried out at a temperature ranging from room temperature (20-25° C.) and the reflux temperature of the suspension obtained by putting the above-mentioned components (i), (ii), (iv), (v), and optionally (iii) in contact, preferably at the reflux temperature of the suspension obtained by putting the above-mentioned components in contact.

According to a preferred embodiment of the present invention, said process can be carried out for a time ranging from 1 hr to 10 hrs, preferably from 1.5 hrs to 8 hrs.

At the end of the above process, the precipitation of the metal alkyl-arene can be obtained in the form of a solid (e.g., by means of an organic solvent such as, for example, n-pentane, n-hexane, n-heptane), or a solution including said metal alkyl-arene, or an oil comprising said metal alkyl-arene.

A further object of the present invention therefore relates to a solution or an oil, comprising said metal alkyl-arene having general formula (I) or (Ia). Said solution and said oil, can be filtered in order to eliminate the aluminium metal in excess. As already specified above, said solution and said oil can be advantageously used for the preparation of solid components of catalyst for the (co)polymerization of α-olefins.

Alternatively, said metal alkyl-arene having general formula (I) or (Ia), can be obtained by means of a process which comprises reacting a metal arene with at least one alkylating agent.

A further object of the present invention therefore relates to a process for the preparation of a metal alkyl-arene having general formula (I) or (Ia) which comprises putting the following components in contact:

(i') at least one metal arene having general formula (VI) or (VIa):

$$M(\eta^6\text{-arene})_2Al_qX_r \quad (VI)$$

$$M(\eta^6\text{-arene})Al_qX_r \quad (VIa)$$

wherein:
M represents zirconium (Zr), hafnium (Hf), or mixtures thereof, preferably zirconium;
arene represents a benzene, or a benzene substituted with from 1 to 6 linear or branched $C_1$-$C_6$ alkyl groups, or mixtures thereof;
X represents a halogen atom selected from chlorine, bromine, fluorine, iodine, preferably chlorine;
q is a number ranging from 2 to 6, preferably 3 when the metal arene has general formula (VI), 2 when the metal arene has general formula (VIa);
r is a number ranging from 8 to 20, preferably 11 when the metal arene has general formula (VI), 8 when the metal arene has general formula (VIa);

(ii') at least one alkylating agent selected from:
metal alkyls having general formula (IV):

$$M_1(R_1)_m \quad (IV)$$

wherein $M_1$ represents aluminium, magnesium, zinc, lithium; $R_1$ represents a linear or branched $C_1$-$C_{20}$, preferably $C_1$-$C_{18}$, alkyl group; m is 1, 2, or 3;
aluminium alkyl chlorides having general formula (V):

$$Al(R_2)_nCl_{3-n} \quad (V)$$

wherein $R_2$ represents a linear or branched $C_1$-$C_{20}$, preferably $C_1$-$C_{18}$, alkyl group; n is 1 or 2.

The zirconium arene having general formula (VI) or (VIa) can be obtained according to processes known in the art, as described, for example, by Troyanov S. et al. in "Synthesis of arene Ti and Zr complexes and their reactivity towards air: crystal structure of [(C₆H₃Me₃)₂Zr(AlCl₄)](Al₂Cl₇) and TiCl₃(OPh)", *Journal of Organometallic Chemistry* (1995), Vol. 494, C4-C7; or in "The synthesis and crystal structure of the π-benzenezirconium(III) bromoaluminate complex {(μ₂-Br)₃[(η-C₆H₆)Zr(μ₂-Br)₂.AlBr₂]₂} (Al₂Br₇).2.5C₆H₆ and the π-benzene-zirconium(II) iodoaluminate complex [(η-C₆H₆)₂Zr((μ₂-I)₂AlI₂](Al₃I₁₀).5C₆H₆", *Organometallic Chemistry in the USSR* (1989), Vol. 2(6), pages 732-736; or in "The synthesis and crystal structure of the π-mesitylenezirconium(II) bromide complexes [(π⁶-C₆H₃Me₃)₂Zr(μ-Br)₂AlBr₂].(Al₂Br₇) and [(η⁶-C₆H₃Me₃)₂Zr(μ-Br)₂.AlBr₂](Al₃OBr₈)", *Organometallic Chemistry in the USSR* (1992), Vol. 5(5), pages 527-530; "Arene Complexes of Titanium and Zirconium in Low Oxidation States: Crystal Structures of β-(η⁶-C₆H₆)Ti(AlI₄)₂, [η⁶-(C₆Me₆)₃Zr₃Br₆] (Al₂OBr₈) (Al₂Br₇).(C₆H₆), [η⁶-C₆H₃Me₃)₃Zr₃Br₆](Al₃OBr₈)₃, and [(η⁶-C₆H₆)₂Zr(AlBr₄)](Al₂Br₇).2(C₆H₆)," *Russian Journal of Coordination Chemistry* (1997), Vol. 23, No. 12, pages 836-843. Alternatively, zirconium arene having general formula (VI) or (VIa) can be obtained according to what is described by Calderazzo F. et al. in the above-mentioned article, or by Pampaloni G. in the review mentioned above.

Said zirconium arene having general formula (VI) or (VIa) can be obtained, for example, by putting the following components in contact, under the reaction conditions indicated in the above processes: metal aluminium, aluminium trichloride, metal tetrachloride and the arene selected. Said components can be reacted at a temperature ranging from room temperature (20° C.-25° C.) and the reflux temperature of the reaction mixture obtained by putting said components in contact. At the end of the reaction, a suspension comprising said metal arene can be obtained, or a biphasic system (reaction raw product) which can be filtered to eliminate the unaltered metal aluminium in excess, obtaining a solution from which said metal arene in the form of a solid is separated, for example, by precipitation in a hydrocarbon solvent, preferably aliphatic (e.g., n-heptane), or it may not be filtered.

For the purposes of the present invention and of the following claims, the wording "at least one metal arene having general formula (VI) or (VIa)" means that either a metal arene in solid form, or the suspension, or the biphasic system (reaction raw product), obtained in the preparation process of said metal arene having general formula (VI) or (VIa) containing said zirconium arene having general formula (VI) or (VIa), can be used.

The above process, which comprises putting components (i') and (ii') in contact, can be carried out by operating at a molar ratio between the metal present in the metal alkyls having general formula (IV), or the aluminium present in the aluminium chlorides having general formula (V), and the metal present in the metal arene having general formula (VI) or (VIa), ranging from 1 to 20, preferably from 1.2 to 15.

The above process, which comprises putting components (i') and (ii') in contact, can be carried out in the presence of an organic solvent, preferably an aliphatic or aromatic hydrocarbon solvent, selected from those described above and under the same operating conditions (i.e. temperature, time) indicated above for the process which comprises putting components (i), (ii), (iv), (v) and optionally (iii), in contact. At the end of said process, the precipitation of the metal alkyl-arene in solid form (e.g., by means of an organic solvent such as, for example, n-pentane, n-hexane, n-heptane), or a solution comprising said metal alkyl-arene, or an oil comprising said metal alkyl-arene, can be obtained.

Some illustrative and non-limiting examples are provided for a better understanding of the present invention and for its embodiment.

EXAMPLES

Reagents and Materials

The reagents and materials used in the following examples of the invention are listed hereunder together with their optional pre-treatments and their producer:
zirconium tetrachloride ($ZrCl_4$) (Aldrich, 99.9%): used as such;
metal aluminium (Al) (Carlo Erba RPE): powder, used as such;
anhydrous aluminium trichloride ($AlCl_3$) (Fluka): used as such;
mesitylene (Aldrich): pure, ≥99%, distilled on sodium (Na) in an inert atmosphere;

benzene (Aldrich): pure, ≥99%, distilled on sodium (Na) in an inert atmosphere;

lithium n-butyl (Li$^n$Bu) (Aldrich): solution 2.5 M in a mixture of hexanes;

lithium sec-butyl (Li$^s$Bu) (Aldrich): solution 1.4 M in cyclohexane;

lithium tert-butyl (Li$^t$Bu) (Aldrich): solution 1.7 M in n-pentane;

lithium iso-butyl (Li$^i$Bu) (Aldrich): solution 1.4 M in toluene;

lithium n-pentyl (Li$^n$pentyl) solution 2.2 M in n-heptane;

magnesium n-butyl-n-octyl [(n-C$_4$H$_9$)$_{1.5}$(n-(C$_8$H$_{17}$)$_{0.5}$Mg] (Chemtura): solution 20% in n-heptane;

magnesium di-n-butyl [(n-C$_4$H$_9$)$_2$Mg] (Aldrich): solution 1 M in n-heptane;

n-pentane (Carlo Erba, RPE): anhydrified by distillation on sodium (Na) in an inert atmosphere;

n-hexane (Carlo Erba, RPE): anhydrified by distillation on sodium (Na) in an inert atmosphere;

n-heptane (Carlo Erba, RPE): anhydrified by distillation on sodium (Na) in an inert atmosphere;

aluminium tri-octyl [Al(n-octyl)$_3$] (Aldrich): used as such;

aluminium tri-ethyl [Al(ethyl)$_3$] (Schering AG): used as such;

aluminium tri-iso-butyl [Al(iso-butyl)$_3$] (Schering AG): used as such;

n-octyl aluminium dichloride (Akzo-Nobel): used as such;

di-ethyl-aluminium chloride [AlCl(ethyl)$_2$] (Chemtura, pure): used as such.

The analyses and characterization methods listed below were used.

Elemental Analysis a) Determination of Zr, Hf, Al, Mg

For the determination of the weight quantity of the metals Zr, Hf, Al and Mg, in the metal alky-arenes object of the present invention, an aliquot weighed exactly, operating in a dry-box under a nitrogen flow, of about 30 mg-50 mg of sample, was placed in a platinum crucible of about 30 ml, together with a mixture of 1 ml of hydrofluoric acid (HF) at 40%, 0.25 ml of sulfuric acid (H$_2$SO$_4$) at 96% and 1 ml of nitric acid (HNO$_3$) at 70%. The crucible was then heated on a plate, increasing the temperature until the appearance of white sulfuric fumes (about 200° C.). The mixture thus obtained was cooled to room temperature (20° C.-25° C.), 1 ml of nitric acid (HNO$_3$) at 70% was added and the mixture was then heated until the appearance of fumes. After repeating the sequence a further two times, a limpid, almost colourless solution was obtained. 1 ml of nitric acid (HNO$_3$) and about 15 ml of water were then cold added and the mixture was then heated to 80° C. for about 30 minutes. The sample thus prepared was diluted with water having a MilliQ purity up to a weight of about 50 g, weighed exactly, to obtain a solution on which analytical instrumental determination was carried out using an ICP-OES spectrometer (optical detection plasma) Thermo Optek IRIS Advantage Duo, by comparison with solutions at a known concentration. For this purpose, a calibration curve was prepared for each analyte, within the range of 0-10 ppm, measuring solutions having a known titre obtained by weight dilution of certified solutions.

The solution of the sample prepared as described above was diluted again by weight so as to obtain concentrations close to those used as reference, before effecting spectrophotometric detection. All the samples were prepared in duplicate. The results were considered acceptable if the single data of the tests in duplicate did not differ by more than 2% relative with respect to their average value.

b) Chlorine Determination

For this purpose, samples of the metal alkyl-arenes, object of the present invention, about 30 mg-50 mg, were weighed exactly in 100 ml glasses in a dry-box under a stream of nitrogen. 2 g of sodium carbonate (Na$_2$CO$_3$) were added and 50 ml of MillQ water were added, outside the dry-box. The mixture was brought to boiling point on a plate under magnetic stirring for about 30 minutes. It was left to cool, sulfuric acid (H$_2$SO$_4$) diluted ⅕ was added until the reaction became acid and the mixture was titrated with silver nitrate (AgNO$_3$) 0.1 N with a potentiometer titrimeter.

c) Determination of the Carbon and Hydrogen

The determination of the carbon and hydrogen in the metal alkyl-arenes, object of the present invention, was carried out by means of a Carlo Erba automatic analyzer Mod. 1106.

UV-Vis Spectroscopy

The UV-Vis analysis was carried out using a Perkin-Elmer Λ-19 double-beam spectrophotometer, with scanning within the range of 300 nm to 850 nm and resolution at 0.5 nm. For this purpose, samples of the metal alkyl-arenes, object of the present invention, were dissolved in an appropriate anhydrous solvent and degassed, at the desired molar concentration. The solutions being examined (about 3 ml) were introduced with the Schlenk technique in an anhydrified argon or nitrogen atmosphere into cells with an optical path of 1 cm specifically modified with a rotaflow stopcock, to allow the charging of the solution in an inert atmosphere and also to ensure a better seal and consequently minimize degradation phenomena by oxidation and/or hydrolysis.

Example 1

Synthesis of Zr($\eta^6$-mesitylene)Al$_2$Cl$_6$(n-butyl)$_2$ and Isolation of the Solid Compound by Reaction of Zirconium Tetrachloride (ZrCl$_4$) and Lithium N-Butyl (Li$^n$Bu)

A suspension of ZrCl$_4$ (0.40 mg, 1.71 mmoles), Al (0.069 g, 2.56 mmoles) and AlCl$_3$ (0.68 g, 5.10 mmoles) in mesitylene (40 ml), was heated to reflux temperature for 3 hours. The system was treated with Li$^n$Bu (1.4 ml of a solution 2.5 M in a mixture of hexanes, 3.5 mmoles). The solution obtained was filtered on a porous septum to eliminate the aluminium metal in excess. The volume of the solvent was reduced by evaporation at reduced pressure and 30 ml of cold n-pentane were added. The suspension obtained was left under stirring for 5 hours at about 10° C., the solvent was then removed by evaporation under vacuum. The addition of cold n-pentane was repeated a second time and, after filtration of the precipitate obtained, 510 mg (46%) of a dark brown solid were isolated. Elemental analysis, chlorine, carbon and hydrogen determination carried out on the solid gave the following elemental atomic ratios: ZrC$_{18}$H$_{33}$Al$_{1.9}$Cl$_{6.2}$.

UV-Vis analysis (mesitylene) revealed the following three bands: at 300 nm (weak), at 372 nm (intense), at 540 nm (weak).

Said solid was also characterized by means of an IR spectrum (reflectance, solid state) showing the following bands: 2952 m, 2916 m, 2871 m, 1618 w, 1461 w, 1411 vw, 1376 w, 1340 vw, 1295 vw, 1267 vw, 1247 w, 1191 w, 1080 w, 1027 vw, 999 vw, 961 vw.

Said solid was also characterized by means of $^1$H-NMR (400 MHz, C$_6$D$_6$): 6.65 (s, C$_6$H$_3$(CH$_3$)$_3$), 2.12 (s, C$_6$H$_3$(CH$_3$)$_3$); 0.36, 0.93, 1.30, 1.40 (br, Bu) ppm.

Said solid was also characterized by means of $^{13}$C-NMR (400 MHz, $C_6D_6$): 138.1, 126.6 ($C_6H_3(CH_3)_3$), 21.3 ($C_6H_3(CH_3)_3$), 1.0, 3.7, 13.9, 30.2 (Bu) ppm.

Example 2

Synthesis of Zr($\eta^6$-mesitylene)$Al_2Cl_6$(sec-butyl)$_2$ and Isolation of the Solid Compound by Reaction of Zirconium Tetrachloride ($ZrCl_4$) and Lithium Sec-Butyl (Li$^s$Bu)

A suspension of $ZrCl_4$ (0.43 g, 1.84 mmoles), Al (0.075 g, 2.78 mmoles) and $AlCl_3$ (0.75 mg, 5.62 mmoles) in mesitylene (40 ml), was heated to reflux temperature for 3 hours. The system was treated with Li$^s$Bu (2.6 ml of a solution 1.4 M cyclohexane, 3.64 mmoles). The solution obtained was filtered on a porous septum to eliminate the aluminium metal in excess. The volume of the solvent was reduced by evaporation at reduced pressure and 30 ml of cold n-pentane were added. The suspension was left under stirring for 5 hours at about 10° C., the solvent was then removed by evaporation under vacuum. The addition of cold n-pentane was repeated a second time and, after filtration of the precipitate obtained, 458 mg (43%) of a brown solid were isolated. Elemental analysis, chlorine, carbon and hydrogen determination carried out on the solid gave the following elemental atomic ratios: $ZrAl_2Cl_{6.1}C_{17}H_{30}$.

UV-Vis analysis (mesitylene) revealed the following three bands: at 308 nm (weak), at 374 nm (intense), at 526 nm (weak).

Example 3

Synthesis of Zr($\eta^6$-mesitylene)$Al_2Cl_6$(n-butyl)$_2$ and Isolation of the Solid Compound by Reaction of Zirconium Tetrachloride ($ZrCl_4$) and Lithium Tert-Butyl (Li$^t$Bu)

A suspension of $ZrCl_4$ (0.44 g, 1.88 mmoles), Al (0.076 g, 2.82 mmoles) and $AlCl_3$ (0.76 g, 5.70 mmoles) in mesitylene (40 ml), was heated to reflux temperature for 3 hours. The system was treated with Li$^t$Bu (2.2 ml of a solution 1.7 M in n-pentane, 3.74 mmoles). The solution obtained was filtered on a porous septum to eliminate the aluminium metal in excess. The volume of the solvent was reduced by evaporation at reduced pressure and 30 ml of cold n-pentane were added. The suspension obtained was left under stirring for 5 hours at about 10° C., the solvent was then removed by evaporation under vacuum. The addition of cold n-pentane was repeated a second time and, after filtration of the precipitate obtained, 551 mg (49%) of a dark brown solid were isolated. Elemental analysis, chlorine, carbon and hydrogen determination carried out on the solid gave the following elemental atomic ratios: $ZrAl_2Cl_{6.1}C_{17}H_{30}$.

UV-Vis analysis (mesitylene) revealed the following three bands: at 306 nm (weak), at 376 nm (intense), at 542 nm (weak).

Example 4

Synthesis of Zr($\eta^6$-mesitylene)$Al_2Cl_6$(n-pentyl)$_2$ and Isolation of the Solid Compound by Reaction of Zirconium Tetrachloride ($ZrCl_4$) and Lithium N-Pentyl (Li$^n$Pentyl)

A suspension of $ZrCl_4$ (0.35 g, 1.50 mmoles), Al (0.060 g, 2.22 mmoles) and $AlCl_3$ (0.60 g, 4.50 mmoles) in mesitylene (40 ml), was heated to reflux temperature for 3 hours. The system was treated with Li$^n$pentyl (1.4 ml of a solution 2.2 M in n-heptane, 3.1 mmoles). The solution obtained was filtered on a porous septum to eliminate the aluminium metal in excess. The volume of the solvent was reduced by evaporation at reduced pressure and 30 ml of cold n-pentane were added. The suspension obtained was left under stirring for 5 hours at about 10° C., the solvent was then removed by evaporation under vacuum. The addition of cold n-pentane was repeated a second time and, after filtration of the precipitate obtained, 512 mg (55%) of a dark brown solid were isolated. Elemental analysis, chlorine, carbon and hydrogen determination carried out on the solid gave the following elemental atomic ratios: $ZrAl_{1.8}Cl_{5.9}C_{19}H_{35}$.

UV-Vis analysis (mesitylene) revealed the following three bands: at 298 nm (weak), at 380 nm (intense), at 530 nm (weak).

Example 5

Synthesis of Zr($\eta^6$-mesitylene)$Al_2Cl_{5.7}(C_{13}H_{27})$ and Isolation of the Compound (Oil) by Reaction of Zirconium Tetrachloride ($ZrCl_4$) and Magnesium N-Butyl-N-Octyl A suspension of $ZrCl_4$ (5.64 g, 24.2 mmoles), Al (0.098 g, 36.30 mmoles) and $AlCl_3$ (9.7 g, 72.75 mmoles) in mesitylene (250 ml) was heated to reflux temperature for 3 hours. The system was treated with magnesium n-butyl-n-octyl (55.30 ml of a solution 20% w/w in n-heptane, 48.4 mmoles). The solution obtained was filtered on a porous septum to eliminate the aluminium metal in excess. The volume of the solvent was reduced by evaporation at reduced pressure and 100 ml of cold n-pentane were added. The suspension obtained was left under stirring for 5 hours at about 10° C., the solvent was then removed by evaporation under vacuum. The addition of cold n-pentane was repeated a second time and, after filtration, the solution was evaporated under vacuum obtaining 10 g of a dark brown oil. Elemental analysis, chlorine, carbon and hydrogen determination carried out on the oil gave the following elemental atomic ratios: $ZrAl_{1.9}Cl_{5.7}C_{22}H_{41}$.

UV-Vis analysis (mesitylene) revealed the following bands: 315 nm (weak), 415 nm (weak), 500 nm (weak).

Said oil was also characterized by means of IR spectrum (a.s.) showing the following bands: 2956 m, 2921 m, 2870 w, 2854 m, 1606 m, 1464 m, 1402 w, 1377 m, 1340 vw, 1295 vw, 1267 vw, 1247 vw, 1141 w, 1064 w, 1037 vw, 999 vw, 961 vw, 835 m, 772 m, 690 m, 674 w, 622 m, 500 w, 438 m, 369 vw, 310 w.

Example 6

Synthesis of Zr($\eta^6$-benzene)$Al_3Cl_9$(n-butyl)$_2$ and Isolation of the Solid Compound by Reaction of Zr($\eta^6$-benzene)$Al_3Cl_{11}$ and Magnesium Di-N-Butyl A solution of Zr($\eta^6$-benzene)$_2(Al_3Cl_{11})$ (2.00 g, 2.78 mmoles) in benzene (100 ml) was treated with magnesium di-n-butyl (6.00 ml of a solution 1 M in n-heptane, 6.00 mmoles) and was left under stirring for 1 hour. The solution obtained was filtered on a porous septum. The volume of the solvent was reduced by evaporation at reduced pressure and 50 ml of cold n-pentane were added. The suspension obtained was left under stirring for 8 hours at about 10° C., the solvent was then removed by evaporation under vacuum. The addition of cold n-pentane was repeated a second time and after filtration of the precipitate obtained, 1 g (47%) of a dark brown solid was isolated. Elemental analysis, chlorine, carbon and hydrogen determination carried out on the solid gave the following elemental atomic ratios: $ZrAl_{2.9}Cl_{8.4}C_{21}H_{35}$.

UV-Vis analysis (benzene) revealed the following bands: 307 nm (weak), 413 nm (weak), 490 nm (weak).

Said solid was also characterized by means of IR spectrum (nujol) showing the following bands: 3083 m, 1606 m, 1525 m, 1324 w, 1064 w, 1037 vw, 999 vw, 884 vw, 788 m, 706 m, 690 m, 674 w, 622 m, 507 w, 494 w, 438 m, 369 vw, 310 w.

Example 7

Synthesis of $Zr(\eta^6$-mesitylene$)Al_2Cl_6$(n-octyl$)_2$ and Isolation of the Compound (Oil) by Reaction of Zirconium Tetrachloride ($ZrCl_4$) and N-Octyl Aluminium Dichloride A suspension of $ZrCl_4$ (3.8 g, 16.3 mmoles), Al (2.6 mg, 97.4 mmoles), n-octyl aluminium dichloride (7.2 ml, 32.5 mmoles) in mesitylene (50 ml), was heated to reflux temperature for 2 hours, under stirring. The solution obtained was filtered on a porous septum to eliminate the aluminium metal in excess. The volume of the solvent was reduced by evaporation at reduced pressure and 40 ml of cold n-pentane were added. The suspension obtained was left under stirring for 8 hours at about 10° C., the solvent was then removed by evaporation under vacuum. The addition of cold n-pentane was repeated a second time and, after filtration, the solvent was removed by evaporation under vacuum obtaining 10 g of a dark brown oil. Elemental analysis, chlorine, carbon and hydrogen determination carried out on the oil gave the following elemental atomic ratios: $ZrAl_{2.2}Cl_{6.7}C_{25}H_{47}$.

UV-Vis analysis (mesitylene) revealed the following band: 520 nm.

Example 8

Synthesis of $Zr(\eta^6$-mesitylene$)Al_2Cl_6$(ethyl$)_2$ and Isolation of the Solid Compound by Reaction of Zirconium Tetrachloride ($ZrCl_4$) and Aluminium Tri-Ethyl [Al(Ethyl)$_3$]

A suspension of $ZrCl_4$ (0.39 g, 1.67 mmoles), Al (0.067 g, 2.48 mmoles) and $AlCl_3$ (0.67 g, 5.02 mmoles) in mesitylene (40 ml), was heated to reflux temperature for 3 hours. The system was treated with Al(ethyl)$_3$ (3.40 mmoles, Al(ethyl)$_3$/Zr=2).

The mixture obtained was filtered on a porous septum to eliminate the aluminium metal in excess. The volume of the solvent was reduced by evaporation at reduced pressure and 30 ml of cold n-pentane were added. The suspension obtained was left under stirring for 10 hours at about 10° C., the solvent was then removed by evaporation under vacuum. The addition of cold n-pentane was repeated a second time and, after filtration of the precipitate obtained, 153 mg (17%) of a dark brown solid were isolated. Elemental analysis, chlorine, carbon and hydrogen determination carried out on the solid gave the following elemental atomic ratios: $ZrAl_{2.1}Cl_{6.2}C_{13}H_{22}$.

UV-Vis analysis (dichloroethane) revealed a weak band at 527 nm.

Example 9

Synthesis of $Zr(\eta^6$-benzene$)Al_2Cl_6$(iso-butyl$)_2$ and Isolation of the Solid Compound by Reaction of Zirconium Tetrachloride ($ZrCl_4$) and Aluminium Tri-Iso-Butyl [Al(Iso-Butyl)$_3$]

A suspension of $ZrCl_4$ (0.47 g, 2.02 mmoles), Al (0.080 g, 2.96 mmoles) and $AlCl_3$ (0.8 g, 6.00 mmoles) in a benzene/mesitylene mixture (40/10 ml), was heated to reflux temperature for 3 hours. The system was treated with Al(iso-butyl)$_3$ (4.10 mmoles, Al(iso-butyl)$_3$/Zr=2).

The mixture obtained was filtered on a porous septum to eliminate the aluminium metal in excess. The volume of the solvent was reduced by evaporation at reduced pressure and 30 ml of cold n-pentane were added. The suspension obtained was left under stirring for 10 hours at about 10° C., the solvent was then removed by evaporation under vacuum. The addition of cold n-pentane was repeated a second time and, after filtration of the precipitate obtained, 335 mg (28%) of a dark brown solid were isolated. Elemental analysis, chlorine, carbon and hydrogen determination carried out on the solid gave the following elemental atomic ratios: $ZrAl_{2.1}Cl_{5.9}C_{17}H_{30}$.

UV-Vis analysis (dichloroethane) revealed a band at 529 nm.

Example 10

Synthesis of $Zr(\eta^6$-benzene$)Al_2Cl_6$(Oct$)_2$ and Isolation of the Solid Compound by Reaction of Zirconium Tetrachloride ($ZrCl_4$) and Aluminium Tri-Octyl [Al(Octyl)$_3$]

A suspension of $ZrCl_4$ (0.53 g, 2.27 mmoles), Al (0.092 g, 3.41 mmoles) and $AlCl_3$ (0.91 g, 6.82 mmoles) in a benzene/mesitylene mixture (40/10 ml), was heated to reflux temperature for 3 hours. The system was treated with a solution at 25% of Al(octyl)$_3$ in n-hexane (9.66 ml, 4.6 mmoles, Al(octyl)$_3$/Zr=2).

The solution obtained was filtered on a porous septum to eliminate the aluminium metal in excess. The volume of the solvent was reduced by evaporation at reduced pressure and 20 ml of cold n-pentane were added. The suspension obtained was left under stirring for 5 hours at about 10° C., the solvent was then removed by evaporation under vacuum. The addition of cold n-pentane was repeated a second time and, after filtration of the precipitate obtained, 978 mg (65%) of a dark brown solid were isolated. Elemental analysis, chlorine, carbon and hydrogen determination carried out on the solid gave the following elemental atomic ratios: $ZrAl_{2.1}Cl_{5.9}C_{17}H_{30}$.

UV-Vis analysis (benzene) revealed a band at 519 nm.

Example 11

Preparation of a Solution of $Zr(\eta^6$-mesitylene$)Al_2Cl_6$(iso-butyl$)_2$ by Reaction of a Suspension Comprising $Zr(\eta^6$-mesitylene$)(AlCl_4)_2$ with Lithium Iso-Butyl (Li$^i$Bu)

A suspension of $ZrCl_4$ (0.35 g, 1.50 mmoles), aluminium in powder form (0.060 g, 2.22 mmoles) and $AlCl_3$ (0.60 g, 5.00 mmoles) in mesitylene (40 ml), was heated to reflux temperature for 5 hours obtaining a purple suspension comprising $Zr(\eta^6$-mesitylene$)$ $(AlCl_4)_2$. The suspension was treated with Li$^i$Bu (2.2 ml of a solution 1.4 M in toluene, 3.08 mmoles, Li$^i$Bu/Zr=2) obtaining the formation of a solid phase consisting of aluminium in excess and a brown solution. After filtration, the brown solution obtained was used as such for the preparation of a solid catalyst component for the (co)polymerization of α-olefins.

Example 12

Preparation of a Solution of $Zr(\eta^6$-mesitylene$)Al_2Cl_6$(ethyl$)_2$ by Reaction of a Suspension Comprising $Zr(\eta^6$-mesitylene$)(AlCl_4)_2$ with Aluminium Tri-Ethyl [Al(ethyl)$_3$]

A suspension of $ZrCl_4$ (0.48 mg, 2.06 mmoles), aluminium in powder form (0.08 g, 2.96 mmoles) and $AlCl_3$ (0.80 g, 6.00 mmoles) in mesitylene (40 ml), was heated to reflux temperature for 5 hours obtaining a purple suspension comprising Zr($\eta^6$-mesitylene)(AlCl$_4$)$_2$. The suspension was treated with Al(ethyl)$_3$ (0.66 ml, 4.03 mmoles, Al(ethyl)$_3$/Zr=2) observing only a partial disappearance of the lower purple-coloured liquid phase. Upon increasing the quantity of aluminium tri-ethyl up to a molar ratio Al(ethyl)$_3$/Zr=10, the formation of a solid phase consisting of aluminium in excess, was observed. After filtration, the purple solution obtained was used as such for the preparation of a solid catalyst component for the (co)polymerization of α-olefins.

Example 13

Preparation of a Solution of Zr($\eta^6$-mesitylene) Al$_2$Cl$_6$(iso-butyl)$_2$ by Reaction of a Suspension Comprising Zr($\eta^6$-mesitylene)(AlCl$_4$)$_2$ with Aluminium Tri-Iso-Butyl [Al(iso-butyl)$_3$]

A suspension of ZrCl$_4$ (0.47 mg, 2.02 mmoles), aluminium in powder form (0.08 g, 2.96 mmoles) and AlCl$_3$ (0.80 g, 6.00 mmoles) in mesitylene (40 ml), was heated to reflux temperature for 5 hours obtaining a purple suspension comprising Zr($\eta^6$-mesitylene)(AlCl$_4$)$_2$. The suspension was treated with Al(iso-butyl)$_3$ (4.00 mmoles, Al(iso-butyl)$_3$/Zr=2) observing only a partial disappearance of the lower purple-coloured liquid phase. Upon increasing the quantity of aluminium tri-iso-butyl up to a molar ratio Al(iso-butyl)$_3$/Zr=5, the formation of a solid phase consisting of aluminium in excess, was observed. After filtration, the purple solution obtained was used as such for the preparation of a solid catalyst component for the (co)polymerization of α-olefins.

Example 14

Preparation of a Solution of Zr($\eta^6$-mesitylene) Al$_2$Cl$_6$(n-octyl)$_2$ by Reaction of a Suspension Comprising Zr($\eta^6$-mesitylene)(AlCl$_4$)$_2$ with Aluminium Tri-Octyl [Al(tri-octyl)$_3$]

A suspension of ZrCl$_4$ (0.42 g, 1.80 mmoles), aluminium in powder form (0.07 g, 2.59 mmoles) and AlCl$_3$ (0.73 g, 5.47 mmoles) in mesitylene (40 ml), was heated to reflux temperature for 5 hours obtaining a purple suspension comprising Zr($\eta^6$-mesitylene)(AlCl$_4$)$_2$. The suspension was treated with a solution at 25% of Al(Octyl)$_3$ in n-hexane (5.70 ml, 2.73 mmoles, Al(Octyl)$_3$/Zr=1.5) observing the formation of a solid phase consisting of aluminium in excess. The solid was recovered by filtration and washed with mesitylene obtaining a grey solid substantially consisting of metal aluminium. After filtration, the purple solution obtained was used as such for the preparation of a solid catalyst component for the (co)polymerization of α-olefins.

Example 15

Preparation of a solution of Zr($\eta^6$-benzene)Al$_2$Cl$_4$(ethyl)$_4$ by Reaction of Zirconium Tetrachloride (ZrCl$_4$) with Di-Ethyl-Aluminium Chloride [AlCl(ethyl)$_2$]

A suspension of ZrCl$_4$ (0.254 g, 1.80 mmoles), aluminium in powder form (0.044 g, 1.63 mmoles) and [AlCl(ethyl)$_2$] (0.788 g, 6.54 mmoles) in benzene (40 ml), was heated to reflux temperature for 3 hours obtaining a suspension comprising a solid phase consisting of aluminium in excess and a brown solution comprising Zr($\eta^6$-benzene)Al$_2$Cl$_4$(ethyl)$_4$. The solid was recovered by filtration and washed with benzene obtaining a grey solid substantially consisting of metal aluminium. After filtration, the brown solution obtained was used as such for the preparation of a solid catalyst component for the (co)polymerization of α-olefins.

The invention claimed is:
1. A metal alkyl-arene having general formula (I) or (Ia):

$$M(\eta^6\text{-arene})_2\text{Al}_q X_r R_s \quad (I)$$

$$M(\eta^6\text{-arene})\text{Al}_q X_r R_s \quad (Ia)$$

wherein:
M represents zirconium (Zr), hafnium (Hf), or mixtures thereof;
arene represents a benzene, or a benzene substituted with from 1 to 6 linear or branched C$_1$-C$_6$ alkyl groups, or mixtures thereof;
X represents a halogen atom selected from the group consisting of chlorine, bromine, fluorine, and iodine;
R represents a linear or branched C$_1$-C$_{15}$ alkyl group;
q is a number ranging from 2 to 6;
r is a number ranging from 1 to 20; and
s is a number ranging from 1 to 6.
2. The metal alkyl-arene according to claim 1, wherein M represents zirconium.
3. The metal alkyl-arene according to claim 1, wherein X represents chlorine.
4. The metal alkyl-arene according to claim 1, wherein q is 3 in the case of the metal alkyl-arene having general formula (I), 2 in the case of the metal alkyl-arene having general formula (Ia).
5. The metal alkyl-arene according to claim 1, wherein r is 9 in the case of the metal alkyl-arene having general formula (I), 6 in the case of the metal alkyl-arene having general formula (Ia).
6. The metal alkyl-arene according to claim 1, wherein s is 2.
7. The metal alkyl-arene according to claim 1, wherein in the metal alkyl-arene having general formula (I) or (Ia), said arene is selected from the croup consisting of: benzene, toluene, ortho-xylene, meta-xylene, para-xylene, 1,2,3-trimethylbenzene, 1,2,4-trimethylbenzene, 1,3,5-trimethylbenzene (mesitylene), hexamethylbenzene, and mixtures thereof.
8. The metal alkyl-arene according to claim 1, wherein in the metal alkyl-arene having general formula (I) or (Ia), said group R is selected from the group consisting of: ethyl, n-propyl, iso-propyl, n-butyl, sec-butyl, tert-butyl, iso-butyl, n-pentyl, n-hexyl, n-heptyl, n-octyl, n-decyl, and n-tridecyl.
9. A process for the preparation of a metal alkyl-arene having general formula (I) or (Ia) according to claim 1, which comprises reacting the following components:
(i) at least one metal halide having general formula (II):

$$MX_4 \quad (II)$$

wherein:
M represents zirconium (Zr), hafnium (Hf), or mixtures thereof;
X represents a halogen atom selected from the group consisting of chlorine, bromine, fluorine, and iodine;
(ii) metallic aluminium;
(iii) optionally, at least one aluminium halide having general formula (III):

$$AlX_3 \quad (III)$$

wherein:
X represents a halogen atom selected from the group consisting of chlorine, bromine, fluorine, and iodine;
(iv) at least one arene;
(v) at least one alkylating agent selected from:
metal alkyls having general formula (IV):

$$M_1(R_1)_m \quad (IV)$$

wherein:
M$_1$ represents aluminium, magnesium, zinc, or lithium;
R$_1$ represents a linear or branched C$_1$-C$_{20}$ alkyl group; m is 1, 2 or 3;
aluminium alkyl chlorides having general formula (V):

$$Al(R_2)_nCl_{3-n}$$

wherein R$_2$ represents a linear or branched C$_1$-C$_{20}$ alkyl group; n is 1 or 2.

10. The process according to claim 9, wherein said process is carried out operating at a molar ratio between the aluminium present in the aluminium halide having general formula (III) and the metal present in the metal halide having general formula (II), ranging from 1 to 4.

11. The process according to claim 9, wherein the molar ratio between the metal present in the metal alkyls having general formula (IV) and the metal present in the metal halide having general formula (II), ranges from 1 to 10.

12. The process according to claim 9, wherein said process is carried out operating at a molar ratio between the aluminium present in the aluminium alkyl chlorides having general formula (V) and the metal present in the metal halide having general formula (II), ranging from 1 to 6.

13. The process according to claim 9, wherein said process is carried out in the presence of an aliphatic or aromatic hydrocarbon solvent.

14. The process according to claim 9, wherein said process is carried out at a temperature ranging from 70° C. to the reflux temperature of the suspension obtained by putting the above components (i), (ii), (iv), (v) and optionally (iii), in contact.

15. The process according to claim 9, wherein said process is carried out for a time ranging from 1 hour to 10 hours.

16. A solution, or oil, comprising at least one metal alkyl-arene having general formula (I) or (Ia) according to claim 1.

17. A process using the solution or oil according to claim 16, for the preparation of solid catalyst components for the (co)polymerization of α-olefins.

18. A process for the preparation of a metal alkyl-arene having general formula (I) or (Ia) which comprises putting the following components in contact:
(i') at least one metal arene having general formula (VI) or (VIa):

$$M(\eta^6\text{-arene})_2Al_qX_r \qquad (VI)$$

$$M(\eta^6\text{-arene})Al_qX_r \qquad (VIa)$$

wherein:
M represents zirconium (Zr), hafnium (Hf), or mixtures thereof;
arene represents a benzene, or a benzene substituted with from 1 to 6 linear or branched C$_1$-C$_6$ alkyl groups, or mixtures thereof;
X represents a halogen atom selected from the group consisting of chlorine, bromine, fluorine, and iodine;
q is a number ranging from 2 to 6;
r is a number ranging from 8 to 20;
(ii') at least one alkylating agent selected from:
metal alkyls having general formula (IV):

$$M_1(R_1)_m \qquad (IV)$$

wherein M$_1$ represents aluminium, magnesium, zinc, or lithium; R$_1$ represents a linear or branched C$_1$-C$_{20}$ alkyl group; m is 1, 2, or 3;
aluminium alkyl chlorides having general formula (V):

$$Al(R_2)_nCl_{3-n} \qquad (V)$$

wherein R$_2$ represents a linear or branched C$_1$-C$_{20}$ alkyl group; n is 1 or 2.

19. The process according to claim 18, wherein said process is carried out operating at a molar ratio between the metal present in the metal alkyls having general formula (IV), or the aluminium present in the aluminium chlorides having general formula (V), and the metal present in the metal arene having general formula (VI) or (VIa), ranging from 1 to 20.

20. The process according to claim 18, wherein said process is carried out in the presence of an aliphatic or aromatic hydrocarbon solvent, under the operating conditions at a temperature ranging from 70° C. to the reflux temperature of the suspension.

* * * * *